United States Patent [19]
Corbett

[11] Patent Number: 5,029,103
[45] Date of Patent: Jul. 2, 1991

[54] CARBON DIOXIDE MONITOR

[75] Inventor: James O. Corbett, Eustis, Fla.

[73] Assignee: The Electron Machine Corporation, Umatilla, Fla.

[21] Appl. No.: 431,770

[22] Filed: Nov. 6, 1989

[51] Int. Cl.$^5$ .................. G01N 25/00; G06F 15/20
[52] U.S. Cl. .................................. 364/497; 73/19.06
[58] Field of Search ............. 364/497, 501, 556, 558, 364/557, 579; 73/19.06, 19.1

[56] References Cited

U.S. PATENT DOCUMENTS

| | | | |
|---|---|---|---|
| 3,673,853 | 7/1972 | Griswold | 73/19 |
| 4,280,183 | 7/1981 | Santi | 364/497 |
| 4,550,590 | 11/1985 | Kesson | 73/19 |
| 4,607,342 | 4/1986 | Seiden | 364/558 |
| 4,673,927 | 6/1987 | Cianciavicchia | 73/19 |
| 4,731,732 | 3/1988 | Warcol | 364/510 |
| 4,745,794 | 5/1988 | Steichen | 73/19.06 |
| 4,799,166 | 1/1989 | Shiono | 364/497 |

FOREIGN PATENT DOCUMENTS

| | | | |
|---|---|---|---|
| 2205446 | 8/1973 | Fed. Rep. of Germany | 73/19.06 |
| 1085825 | 10/1967 | United Kingdom | 72/19.06 |

Primary Examiner—Parshotam S. Lall
Assistant Examiner—Ellis B. Ramirez
Attorney, Agent, or Firm—Shlesinger, Arkwright & Garvey

[57] ABSTRACT

An apparatus for monitoring the concentration of dissolved gas in a liquid line comprises a heating element for causing the liquid in the line to boil at a localized point, a thermistor for measuring the temperature at the localized point at the instant of boiling, a pressure transducer for measuring the pressure of the line, and a programmable microprocessor for processing the temperature and pressure data provided by said temperature and pressure measuring means to determine the concentration of the dissolved gas in the liquid line.

27 Claims, 5 Drawing Sheets

CARBON DIOXIDE MONITOR

FIELD OF THE INVENTION

The present invention relates to a device for determining the concentration of dissolved gas in a liquid line, and particularly to determining the concentration of carbon dioxide in a beverage product line as related to the soft drink industry and other beverage industries.

BACKGROUND OF THE INVENTION

In the prior art, the concentration of carbon dioxide in a carbonated liquid beverage is typically measured by obtaining a sealed container such as a can or a bottle filled with the carbonated liquid. The carbonated liquid comes to equilibrium with the gas phase above the liquid and the equilibrium pressure is directly related to the carbon dioxide content of the liquid and the liquid temperature. The carbon dioxide content of the beverage can be determined by measuring the temperature and pressure in the container and applying a mathematical relationship which is dependent on the temperature and pressure of the container, including its contents and other chemical properties of the beverage. This mathematical relationship has been determined empirically. However, the method just described is not applicable in a typical high speed bottling or canning line which runs at hundreds of cans a minute. A procedure in which a container is removed and then measured would allow many containers to be filled before an adjustment could be made for the carbonation level of the beverage.

The carbonated beverage industry presently utilizes product lines which are maintained at near freezing in order to better control the level of carbon dioxide in the lines. Because of the expense of cooling the lines, the trend has been to go to room temperature. However, maintaining a constant level of carbonization in the lines at room temperature with presently available instrumentations and procedures is not without any problems. Several factors contribute to the problems. For example, at higher product temperature, the carbon dioxide pressure is necessarily increased. Also, the carbonization level between one type of product, such as a cola is only slightly different but of critical importance from another type of product, such as an orange drink, thus making control even more difficult.

The present invention provides a solution to the above-mentioned problems.

OBJECTS AND SUMMARY OF THE INVENTION

It is therefore an object of the present invention to provide an apparatus for automatically measuring the concentration of dissolved carbon dioxide in a beverage product line before the beverage is bottled or canned so that adjustments to the gas concentration can be made if necessary.

It is another object of the present invention to provide an apparatus which can be used in a beverage product line operated at room temperature.

It is still another object of the present invention to insure a uniform beverage product which has a consistent level of carbon dioxide present in each can or bottle.

It is yet another object of the present invention to eliminate the waste and inefficiency involved in discarding a batch of canned or bottled product when the carbon dioxide level is tested after the canning or bottling process has been done.

It is another object of the present invention to provide an apparatus for monitoring the concentration of dissolved gas in a liquid line without completely isolating a portion of the liquid and allowing the liquid to reach an equilibrium condition with its vapor phase.

It is still another object of the present invention to provide an apparatus for automatically measuring the concentration of dissolved gas in a liquid line in a high speed bottling or canning operation.

It is still further another object of the present invention to provide an apparatus for remote, in-line and substantially real-time measurement of the concentration of a gas in a liquid line.

It is another object of the present invention to provide an apparatus which provides a direct readout of the concentration of dissolved gas in a liquid line.

In summary, the present invention provides an in-line apparatus for continuously monitoring the concentration of dissolved carbon dioxide in a beverage product in a high speed production line before the beverage is bottled or canned so that adjustments to the gas concentration can be made if necessary, thereby avoiding waste and delay in the production process.

BRIEF DESCRIPTIONS OF THE DRAWINGS

DETAILED DESCRIPTION OF THE INVENTION

FIG. 1

Figure 1:
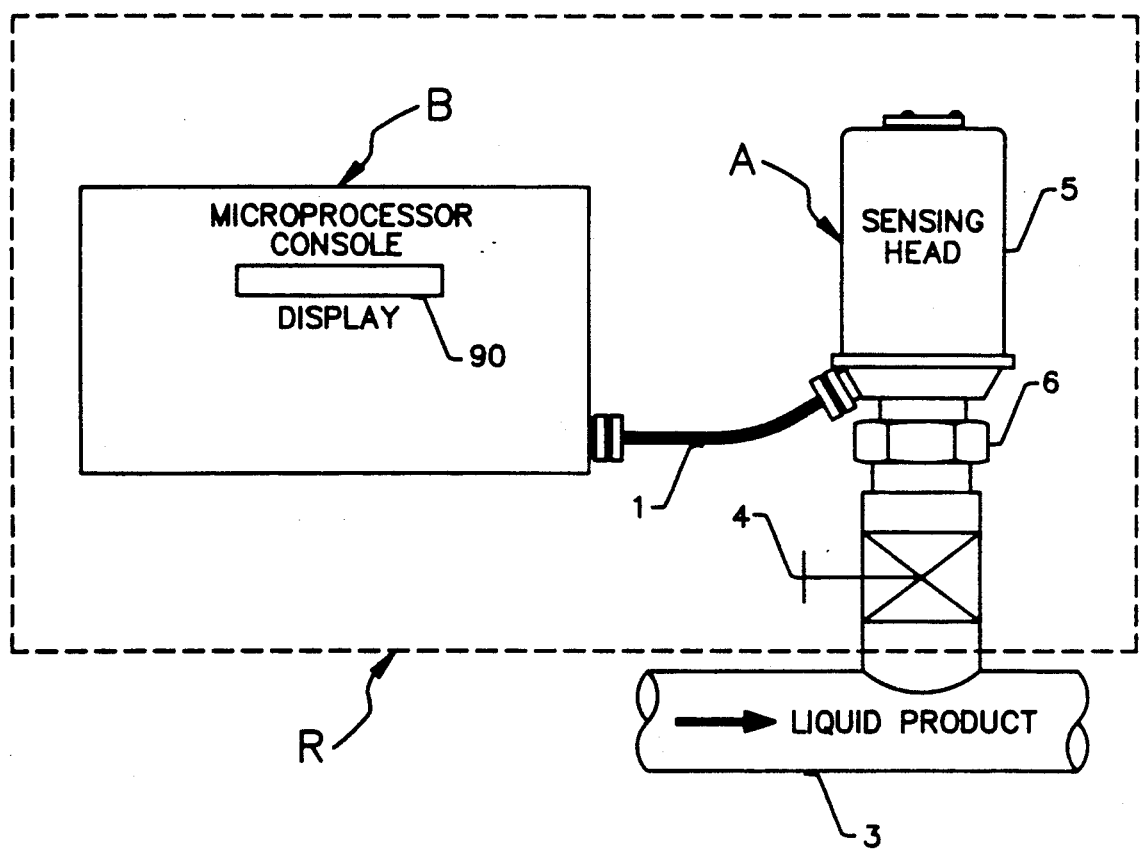
FIG. 1 is a schematic, fragmentary, top view of the present invention in a typical installation.

A carbon dioxide monitoring apparatus R is disclosed in FIG. 1 in a typical installation. The apparatus R includes a sensing head A and a microprocessor console B connected thereto by cable 1. The sensing head A is hooked up to a valve 4 which is connected to a liquid product line 3. The cutoff valve 4 conveniently permits removal of the sensing head A without shutting down and disrupting the liquid product line 3. The valve 4 is normally open during operation.

The sensing head A provides for sensing the temperature and pressure in the liquid line 3, as will be described in greater detail below. The microprocessor console B provides for processing the temperature and pressure information generated by the sensing head A in order to determine and display the concentration of the $CO_2$ in terms of the volume of the liquid, preferably as a ratio of volume of the liquid line to the volume of $CO_2$.

The sensing head A includes a housing 5 and means 6 for appropriately securing the sensing head A to the valve 4.

FIG. 2

The monitoring device A includes a copper tube 7 with a silver probe 8 at the end thereof and a probe tip 9 directly in communication with the liquid in the valve 4. The securing means 6 provides appropriate sealing means (not shown) to prevent leakage of the liquid from the valve 4. A heating element 12 is operably associated with the copper tube 7 such that the heat generated by the heating element 12 is transferred to the copper tube 7. The silver probe 8 in turn transfers the heat from the copper tube 7 to the liquid in the valve 4. The heating element 12 causes the probe tip 9 to become sufficiently hot to cause the liquid adjacent thereto to boil.

A thermistor 16 embedded in the probe tip 9 provides means for measuring the temperature of the probe tip 9.

Figure 2:
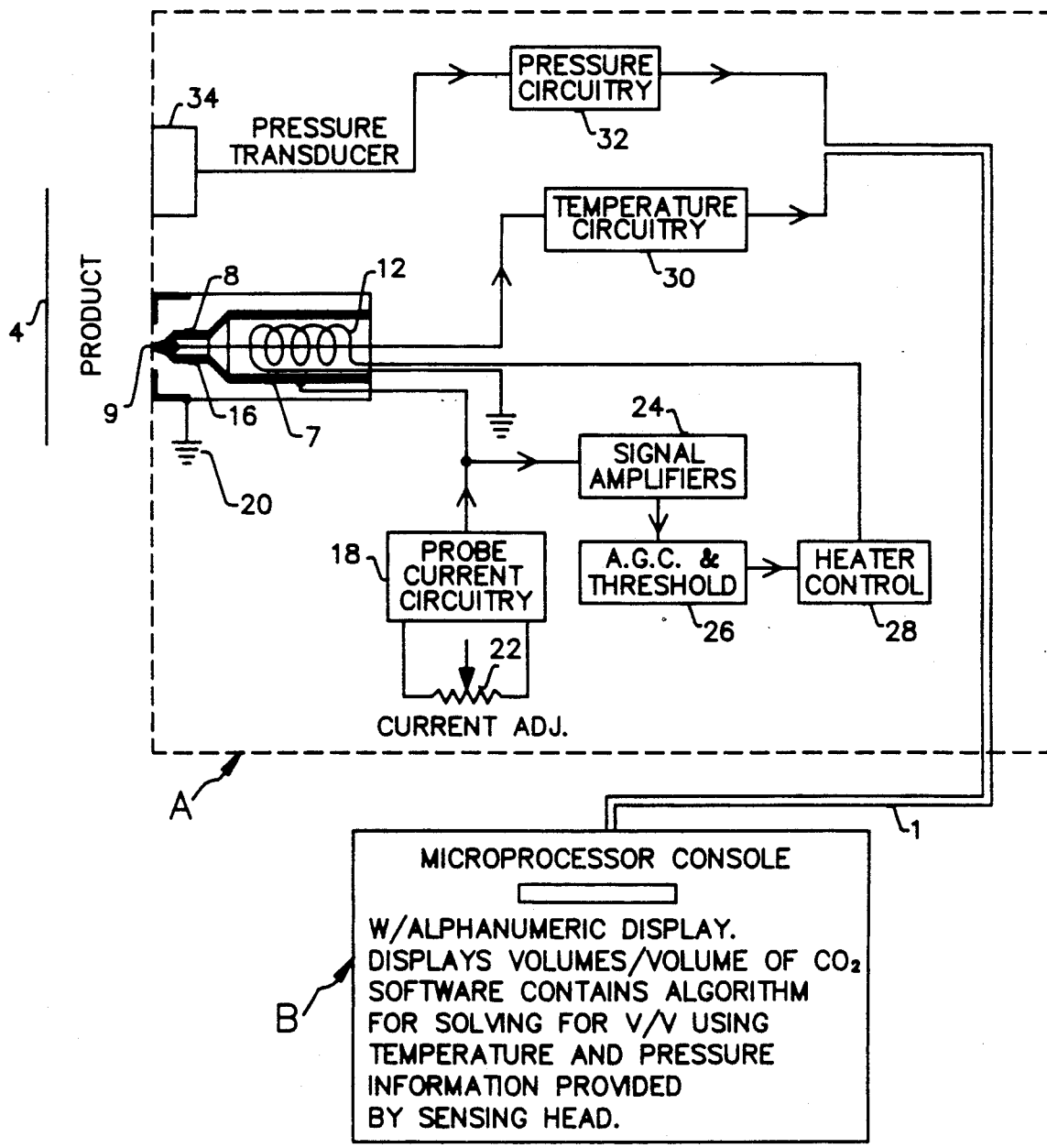
FIG. 2 is a schematic functional block diagram of a sensing head used in the present invention, with portions thereof shown in cross-section.

A probe current circuitry 18 applies either a constant current or constant voltage signal to the probe tip 9. The signal path is from the probe tip 9 through the liquid and to ground 20 which is located in near proximity to the probe tip 9, as best shown in FIG. 2. The probe current circuitry 18 includes adjusting means 22.

The conductivity of the liquid adjacent the probe tip 9 changes as boiling occurs when the probe tip 9 is heated up sufficiently to cause the liquid to boil. Boiling raises the impedance across the probe tip 9, since the bubbles released by boiling isolate the probe tip 9 from the surrounding liquid. Signal amplifiers circuitry 24 amplifies the amplitude of the signal across the probe tip 9. The signal is normally small in amplitude in the absence of boiling since the probe tip 9 is in constant contact with the liquid. However, when boiling occurs, the signal path is disrupted by the release of $CO_2$, thus causing large changes in conductivity, thus affecting the signal amplitude. For example, the voltage across the probe tip 9 could be 2.5 V with no boiling and have 5 V or greater excursions when boiling is occurring.

An automatic gain control and threshold circuitry 26 rectifies the signal from the signal amplifiers circuitry 24 and compares the rectified signal with a preset adjustable reference. The resulting difference signal is then sent to a heater control circuitry 28 which operates the heating element 12 ON/OFF depending on the signal output from the automatic gain control and threshold circuitry 26. When the temperature of the probe tip 9 reaches the boiling point of the liquid, the signal across the probe tip 9 becomes much larger in amplitude in response to the level of boiling occurring. The larger amplitude signal in turn shuts off the heating element 12. As boiling subsides, the signal once again diminishes in amplitude until the circuit demands the heating element 12 to turn on again. The response of the automatic gain control and threshold circuitry 26 is such that the heating element 12 is turned ON and OFF very quickly. The thermal mass of the probe assembly including the copper tube 6 and the silver probe 8 is such as to cause the temperature of the probe tip 9 to be controlled over a very narrow band, typically less than 1° C. The temperature at which boiling occurs is a function of pressure and the $CO_2$ level in the liquid.

Temperature circuitry 30 provides a voltage which varies linearly with respect to the temperature of the probe tip 9. The voltage output of the temperature circuitry 30 is then fed to the microprocessor console B for processing.

Pressure circuitry 32 provides a voltage from a pressure transducer 34, which voltage varies linearly with the liquid pressure. The pressure transducer 34 measures the pressure of the liquid in the valve 4. The output of the pressure circuitry 32 is fed through the microprocessor console B for further processing.

The microprocessor console B also provides an alphanumeric display for indicating the $CO_2$ level in the liquid line in terms of volumes of the liquid per volume of $CO_2$. The microprocessor console B uses an algorithm for solving the volume ratio using the temperature and pressure information provided by the sensing head A.

FIG. 3

The probe current circuitry 18, the signal amplifiers circuitry 24, the automatic gain control and threshold circuitry 26 and the heater control circuitry 28 will now be described in greater detail.

Figure 3:
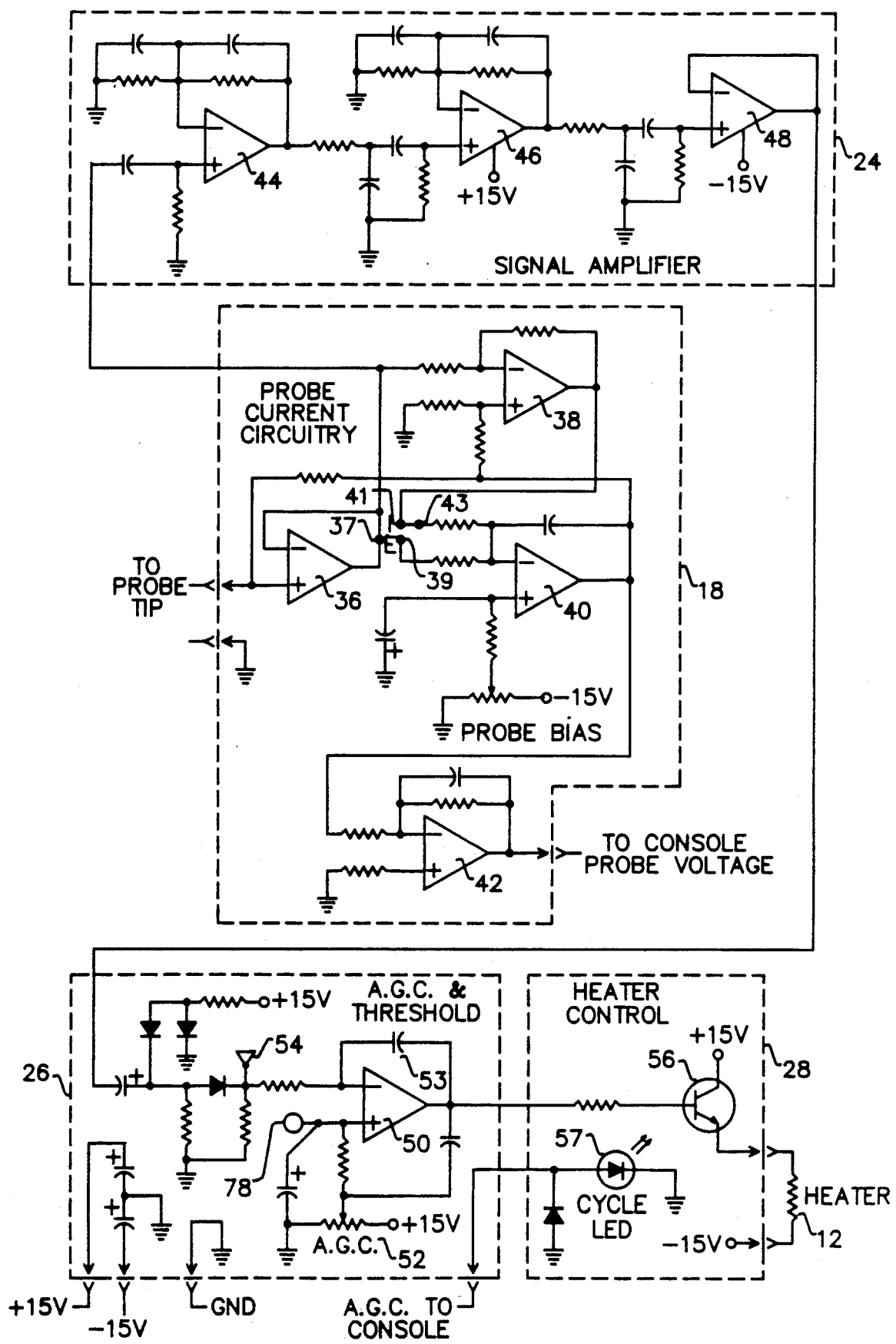
FIG. 3 is a schematic circuit diagram according to the present invention for controlling a heater used in the present invention.

Referring to FIG. 3, the probe current circuitry 18 includes a buffer 36 to prevent loading the signal from the probe 8. Amplifier 38 and its associated circuit components provide the constant current signal for the probe 8. Amplifier 40 and its associated components provide the constant voltage signal for the probe 8. Jumper connections 37, 39, 41 and 43 advantageously provide a user with the option of either selecting a constant current or constant voltage signal for the probe 8. Connecting jumper connections 37 and 39 together provides a constant voltage signal, while connecting jumper connections 41 and 43 provides a constant current signal. Preferably, the constant voltage mode is used. Inverting buffer 42 provides the microprocessor console B with the value in DC volts of the probe voltage for diagnostic purposes.

The signal amplifiers circuitry 24 includes AC amplifiers 44 and 46 and their associated circuit components which condition the signal from the probe current circuitry 18 for rectification in the automatic gain control and threshold circuitry 26. Amplifier 48 and its associated circuit components further attenuate unwanted frequencies and buffer the signal prior to rectification. The signal as detected at the probe 8 typically has some noise associated with it. Therefore, the signal amplifiers circuitry 24 is designed to attenuate unwanted frequencies and amplify the frequency in the band of the signal. The signal generated by the boiling $CO_2$ is typically around 15 Hz. The signal amplifiers circuitry 24 attenuates the signal rapidly above 20 Hz and below 1 Hz.

The automatic gain control and threshold circuitry 26 includes an amplifier 50 and its associated circuit components. The circuitry 26 rectifies the amplified signal from the signal amplifiers circuitry 24 and compares it against a reference voltage which may be adjusted by means of potentiometer 52. Since the amplifier 50 has no resistive feedback, but only capacitive feedback, the output of the amplifier 50 integrates towards saturation either positive or negative depending on whether the voltage on the inverting input of the amplifier 50 is greater or less than that on the non-inverting input. If the voltage is greater at the inverting input, the output of the amplifier 50 goes negative, thereby turning OFF the heating element 12. If the voltage at the inverting input is less than the non-inverting input, then the output of the amplifier 50 goes positive, thereby turning ON the heating element 12.

The rectified DC voltage measured at test point 54 is dependent on the amplitude and the frequency of the signal, with the components selected to provide best performance for the present application. When the probe 8 is too cold to allow the $CO_2$ to boil, the signal is nonexistent. Therefore, the voltage at the inverting input of the amplifier 50 will be less than the voltage at the non-inverting input, causing the heating element 12 to turn ON. When the boiling becomes so great that the voltage at the inverting input exceeds the voltage at the non-inverting input, the heating element 12 turns OFF. In actual operation, the heating element 12 is turned ON and OFF very often. Preferably, the physical mass of the probe assembly is selected to slow down the heating and cooling to the probe 8 so that the boiling point is controlled typically within less than 1° C. A feedback capacitor 53 across the amplifier 50 may also be used to slow down the heating and cooling to the probe 8. A larger value of the capacitor 53 will provide a longer integration time, thereby slowing the rise or fall of the voltage across the heater 12 as the heater 12 is turned ON or OFF and permitting the heater to operate about an average voltage level.

The heater control circuitry 28 includes a transistor 56 for switching the current ON and OFF to the heating element 12, depending on the output of the automatic gain control and threshold circuitry 26. A light emitting diode 57 provides a visual indication of the operation of the heating element 12.

FIG. 4

The temperature circuitry 30 will now be described in greater detail. The temperature circuitry 30 is designed to convert to DC voltage the resistance change provided by the precision linear thermistor 16 disposed within the probe 8. The relationship is typically 0°–150° C. equals 0–10 volts DC. A precision voltage regulator 58 preferably provides an output of 2.5 volts DC. A follower 60 takes the output of the voltage regulator 58 and preferably generates an output of 2.0 volts DC due to the resistor divider on its non-inverting input. Follower 62 preferably provides an output of 1.73 volts DC due to its resistor divider connected to its non-inverting input. Follower 64 preferably provides an output of 1.73 volts DC when the thermistor 16 is at 0° C. due to a resistor divider formed by resistor 66, thermistor 16 and resistor 68. Therefore, the output of amplifier 70 will be 0 volt when the thermistor 16 is sensing 0° C. The gain of the amplifier 70 is preferably set at 9.349 to accommodate the voltage change on the input of the follower 64 at 150° C. The output of the amplifier 70 is 10 volts at 150° C. The relationship of voltage against temperature is preferably linear over the entire range. Amplifier 72 provides the purpose of limiting the temperature of the probe 8. A light emitting diode 74 indicates the condition of over temperature. Point 76 is tied back to point 78 in the automatic gain control and threshold circuitry 26, as best shown in FIG. 3, and causes the input of the amplifier 50 at its non-inverting input to go negative if the temperature of the probe 16 preferably exceeds 150° C., thus turning off the heating element 12 to keep the probe 8 from becoming damaged due to excessive heating, such as might be experienced when the product line 3 is empty and no signal can be generated.

FIG. 5

Figure 4:
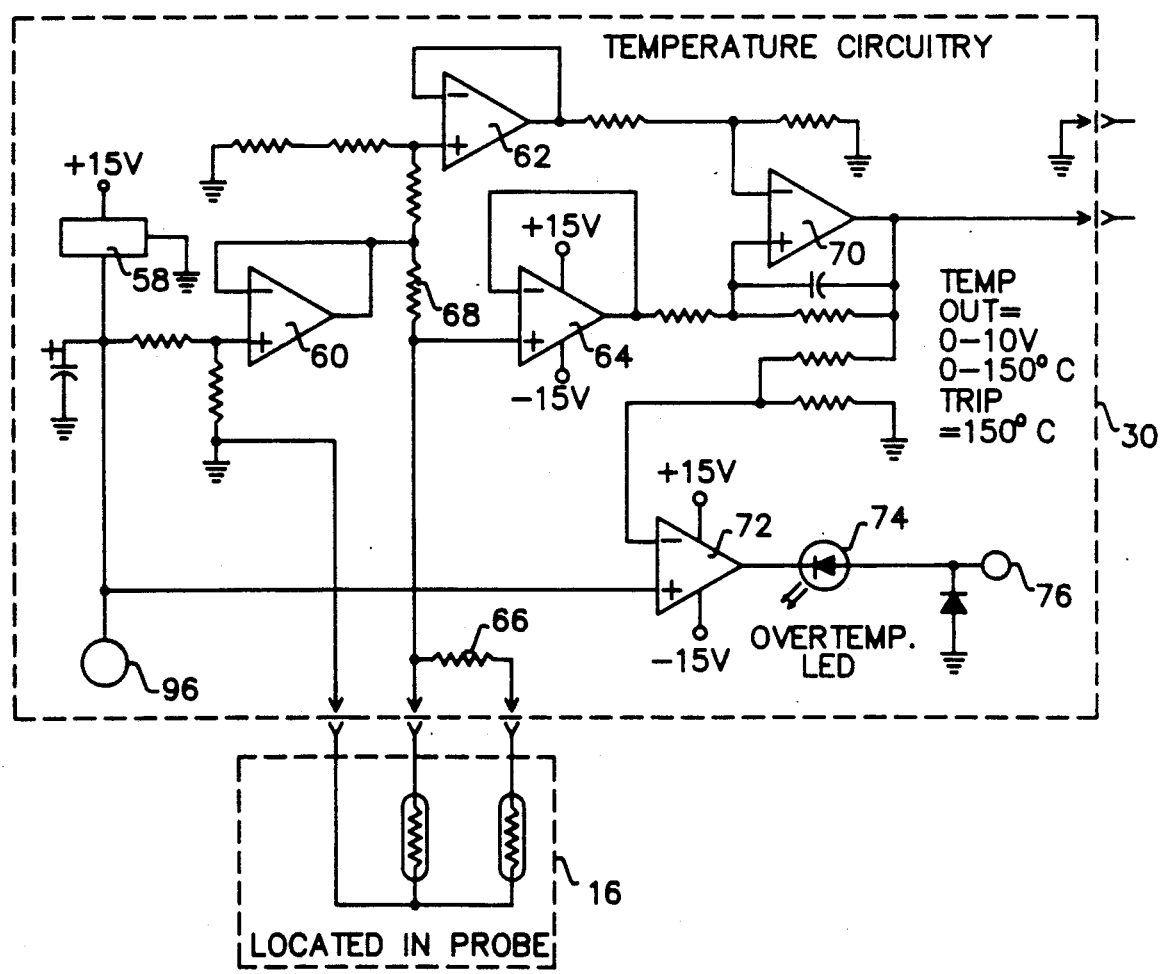
FIG. 4 is a schematic circuit diagram according to the present invention for measuring the boiling temperature of a liquid line.
Figure 5:
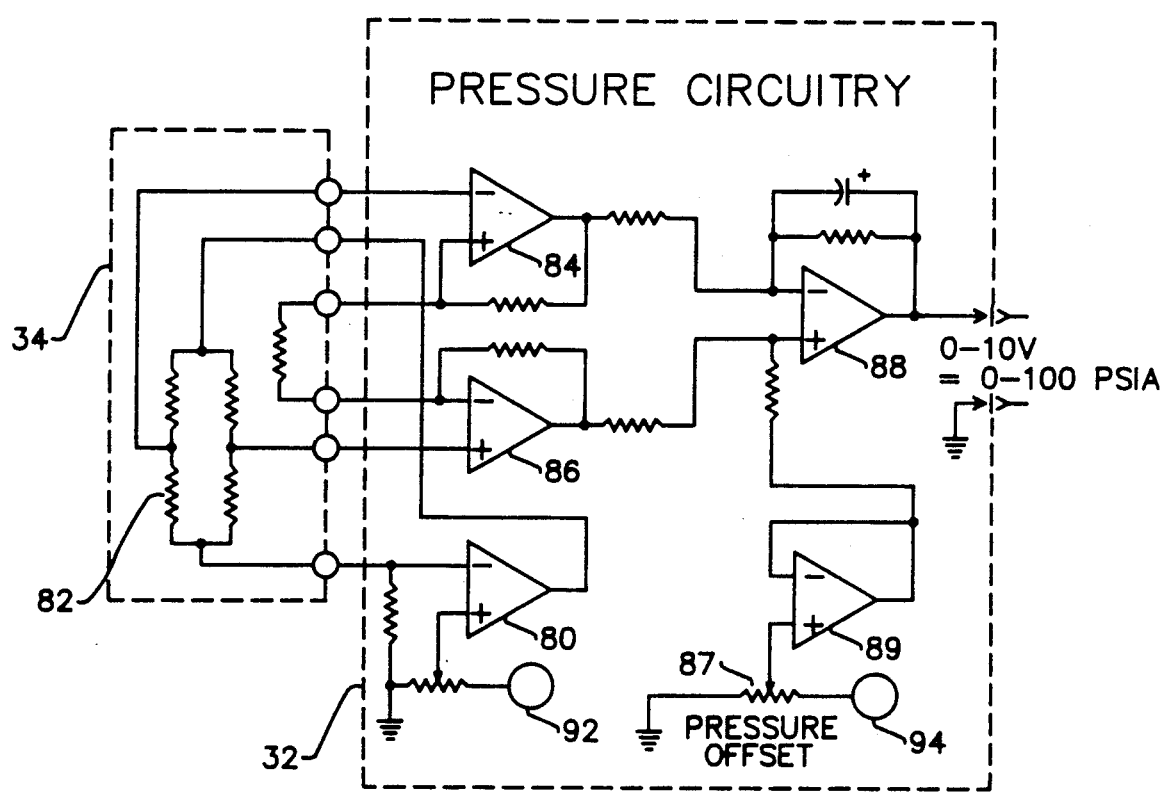
FIG. 5 is a schematic circuit diagram according to the present invention for measuring the pressure of a liquid line.

The pressure circuitry 32 includes an amplifier 80 which is configured to supply an adjustable, constant current to a pressure transducer bridge circuit 82. Amplifiers 84 and 86 are configured to measure and amplify the differential output of the transducer bridge circuit 82. Amplifier 88 amplifies the differential signal for the appropriate gain to provide an output of 0–10 volts equal to 0–100 p.s.i.a. Potentiometer 87 and buffer 89 provide means for adjusting the output of the amplifier 88. Points 92 and 94 are connected to a reference point 96 in FIG. 4.

The microprocessor console B takes the temperature and pressure information from the monitoring device A to generate a readout in display 90 corresponding to the $CO_2$ concentration in the liquid line 2, as best shown in FIG. 2. Preferably, the algorithm for determining the concentration of dissolved carbon dioxide is:

Vol. of liquid/vol. of
$CO_2 = [PA/14.7]*A - [PT - B]*C$, where PA is absolute pressure as measured in the liquid line, A is a variable which is presently set at 1.0, PT is probe temperature in degree centigrade, B is a variable which is presently set at 74 (varies with product), and C is a variable which is presently set at 0.10.

The apparatus R is preferably multi-range and calibrated for use for a group of beverage products.

During operation, there is adequate exchange of liquid between the valve 4 and line 3 to permit accurate measurement of the gas content of the liquid line 3 by measuring the liquid in the valve 4. The sensing head A is normally installed at a slight angle below the horizontal through the product line 3, with the probe tip 9 slightly elevated from the remainder of the sensing head A to allow any trapped bubbles to flow up into the product line 3 and be swept away on down the line, thereby preventing the creation of any noise in the area of the probe tip 9.

While the present invention is disclosed for monitoring the carbon dioxide concentration in a beverage product line, it should be understood to a person skilled in the art it also can be used for other types of dissolved gas amenable to boiling in a liquid line.

While this invention has been described as having preferred design, it is understood that art it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

I claim:
1. An apparatus for monitoring the concentration of dissolved gas in a liquid line, comprising:
   a) means for boiling the liquid at a localized point in the liquid line;
   b) means for detecting the occurrence of boiling in the liquid line;
   c) means for measuring the temperature at the localized point at the instant of boiling;
   d) means for measuring the pressure of the liquid line; and
   e) means for processing the temperature and pressure data provided by said temperature and pressure measuring means, respectively, to determine the concentration of the dissolved gas in the liquid line, thereby permitting adjustments to be made to the gas concentration as appropriate.
2. An apparatus as in claim 1, wherein:

a) said boiling means includes means for detecting a change in conductivity of the liquid when boiling occurs.

3. An apparatus as in claim 2, wherein:
a) said conductivity detecting means includes means for maintaining a constant signal through the liquid and for comparing the signal to a reference value to thereby indicate change in the conductivity of the liquid in the localized point when boiling occurs.

4. An apparatus as in claim 3, wherein:
a) said conductivity detecting means includes means for automatically operating said boiling means such that said boiling means is turned off when boiling occurs and turned on when boiling stops.

5. An apparatus as in claim 1, wherein:
a) said boiling means includes a probe tip in contact with the liquid; and
b) said boiling detecting means includes means for providing a constant signal through the liquid and said probe tip and for detecting any change in the signal due to the formation of bubbles on said probe tip when boiling occurs.

6. An apparatus as in claim 1, wherein:
a) said boiling means includes means for heating the liquid at the localized point in the liquid line.

7. An apparatus as in claim 6, wherein said boiling means comprises:
a) a heat conducting tube operably associated with said heating means;
b) a probe tip operably associated with said tube; and
c) said probe tip is in contact with the liquid in the liquid line.

8. An apparatus as in claim 7, wherein:
a) said heat conducting tube includes copper; and
b) said probe tip includes silver.

9. An apparatus as in claim 5, wherein:
a) said temperature measuring means includes a thermistor operably associated with said probe tip.

10. An apparatus as in claim 9, wherein:
a) said temperature measuring means includes circuit means operably associated with said thermistor for providing a linear output signal proportional to the temperature of said probe tip.

11. An apparatus as in claim 10, wherein:
a) said boiling means includes means for heating the liquid; and
b) means for turning off said heating means when the temperature of said probe tip exceeds a preselected upper limit.

12. An apparatus as in claim 1, wherein:
a) said pressure measuring means includes a pressure transducer.

13. An apparatus as in claim 12, wherein:
a) said pressure measuring means includes circuit means operably associated with said pressure transducer for providing a linear output signal proportional to the pressure of the liquid line.

14. An apparatus as in claim 1, wherein:
a) said processing means is a programmable microprocessor.

15. An apparatus as in claim 14, wherein:
a) said microprocessor includes means for indicating the calculated concentration of dissolved gas in the liquid line.

16. An apparatus for monitoring the concentration of dissolved gas in a liquid line, comprising:
a) a heat conducting probe tip in contact with the liquid in the liquid line;
b) means for heating said probe tip to bring the liquid adjacent said probe tip to a boil;
c) means for detecting the occurrence of boiling at said probe tip;
d) means for measuring the temperature at said probe tip at the instant of boiling;
e) means for measuring the pressure of the liquid line; and
f) a programmable microprocessor means operably associated with said temperature measuring means and said pressure measuring means for processing the temperature and pressure data therefrom to determine the concentration of the dissolved gas in the liquid line.

17. An apparatus as in claim 16, wherein:
a) said boiling detecting means includes means for detecting a change in conductivity of the liquid adjacent said probe tip due to boiling; and
b) means operably associated with said boiling detecting means for automatically operating said heating means such that said heating means is turned off when boiling occurs and turned on when boiling stops.

18. An apparatus as in claim 16, wherein:
a) said heating means includes a heating element operably associated with said probe tip.

19. An apparatus as in claim 16, wherein:
a) said temperature measuring means includes a thermistor operably associated with said probe tip.

20. An apparatus as in claim 16, wherein:
a) said pressure measuring means includes a pressure transducer operably associated with the liquid line.

21. A method for maintaining the concentration of dissolved gas in a liquid line at a preselected level, comprising the steps of:
a) boiling the liquid at a localized point in the liquid line;
b) detecting the occurrence of boiling at the localized point;
c) measuring the temperature at the localized point at the instant of boiling;
d) measuring the pressure in the liquid line;
e) deriving the gas concentration in the liquid line from the temperature and pressure measurements; and
f) adjusting the concentration of dissolved gas in the liquid line to the preselected level if necessary.

22. A method as in claim 16, wherein said step of boiling includes the steps of:
a) providing a probe tip in contact with the liquid in the liquid line; and
b) applying heat to the probe tip until boiling occurs.

23. A method as in claim 21, wherein said step of detecting the occurrence of boiling includes the steps of:
a) maintaining a signal through the liquid and the probe tip; and
b) detecting any change in the signal due to change in conductivity of the liquid when boiling occurs.

24. A method as in claim 21, and including the step of:
a) providing a heating element for the probe tip; and
b) automatically operating the heating element off and on when boiling occurs and when boiling stops, respectively.

25. A method as in claim 21, wherein:
a) said step of measuring the temperature is performed by a thermistor.

26. A method as in claim 21, wherein:
a) said step of measuring the pressure is performed by a pressure transducer.

27. A method as in claim 21, wherein:
a) said step of deriving the gas concentration is performed by a programmable microprocessor.

* * * * *